(12) United States Patent
Kida (10) Patent No.: US 7,926,324 B2
(45) Date of Patent: Apr. 19, 2011

(54) APPARATUS FOR INSPECTING VENTILATION OF FILTER CIGARETTES

(75) Inventor: Shinzo Kida, Tokyo (JP)

(73) Assignee: Japan Tobacco Inc, Tokyo (JP)

( * ) Notice: Subject to any disclaimer, the term of this patent is extended or adjusted under 35 U.S.C. 154(b) by 321 days.

(21) Appl. No.: 11/798,003

(22) Filed: May 9, 2007

(65) Prior Publication Data

US 2007/0209670 A1 Sep. 13, 2007

Related U.S. Application Data (63) Continuation of application No. PCT/JP2005/020097, filed on Nov. 1, 2005.

(30) Foreign Application Priority Data

Nov. 10, 2004 (JP) .................................. 2004-326630

(51) Int. Cl.
*G01M 3/02* (2006.01)

(52) U.S. Cl. ........................................................... 73/37

(58) Field of Classification Search .................. 73/37, 38
See application file for complete search history.

(56) References Cited

U.S. PATENT DOCUMENTS

| | | |
|---|---|---|
| 4,426,567 A | 1/1984 | Gugliotti et al. |
| 4,517,829 A | 5/1985 | Krappitz et al. |
| 4,528,841 A | 7/1985 | Siems et al. |
| 4,888,977 A | 12/1989 | Chehab et al. |
| 5,471,866 A | 12/1995 | Griffiths et al. |
| 5,490,526 A | 2/1996 | Irikura et al. |
| 6,134,948 A | 10/2000 | Fuchigami et al. |
| 6,397,663 B1 | 6/2002 | Chatelet |

FOREIGN PATENT DOCUMENTS

| | | |
|---|---|---|
| DE | 44 00 212 A1 | 7/1994 |
| DE | 198 55 747 A1 | 6/2000 |
| JP | 57-105179 A | 6/1982 |
| JP | 1-309673 A | 12/1989 |
| JP | 5-37628 B2 | 6/1993 |
| JP | 6-66713 A | 3/1994 |
| JP | 6-277031 A | 10/1994 |
| JP | 2000-39392 A | 2/2000 |
| RU | 2 145 177 C1 | 10/2000 |
| SU | 272925 A1 | 1/1970 |
| SU | 328613 A1 | 1/1972 |

*Primary Examiner* — Hezron Williams
*Assistant Examiner* — Alex Devito
(74) *Attorney, Agent, or Firm* — Birch, Stewart, Kolasch & Birch, LLP (57) ABSTRACT

An apparatus for inspecting ventilation of filter cigarettes FT has a plate-like packing 18a. The packing 18a covers the opening of a movable cylinder 10 and is relatively pressed with the end face of a filter cigarette FT. The packing 18a includes a hole 18c positioned to coincide with the center of the end face against the packing, an inner circular area 18f surrounding the hole 18c, and an outer circular area 18g surrounding the inner circular area 18f. The outer circular area 18g is elastically deformed more easily than the inner circular area 18f and is brought into tight contact with the outer circumferential edge of the end face pressed against the packing.

8 Claims, 6 Drawing Sheets

APPARATUS FOR INSPECTING VENTILATION OF FILTER CIGARETTES

This application is a Continuation of copending PCT International Application No. PCT/JP2005/020097 filed on Nov. 1, 2005, which designated the United States, and on which priority is claimed under 35 U.S.C. §120. This application also claims priority under 35 U.S.C. §119(a) on Patent Application No(s). 2004-326630 filed in Japan on Nov. 10, 2004. The entire contents of each of the above documents is hereby incorporated by reference.

TECHNICAL FIELD

The present invention relates to an inspecting apparatus that measures the ventilation of filter cigarettes, and more specifically to an inspecting apparatus suitable for measurement of filter ventilation.

BACKGROUND ART

Filters of filter cigarettes each have a rod-like filter material and a wrapping material in which the filter material is wrapped. There is a filter having apertures in its wrapping material. When a filter cigarette having a filter with apertures is smoked, air flows into the filter through these apertures, and smoke from the cigarette is therefore diluted. This reduces nicotine and tar contained in the smoke, so that the smoker can enjoy a light flavor.

The ratio of the amount of air that flows in through the apertures to the amount of smoke that the smoker draws in is called filter ventilation (hereinafter, also simply referred to as $V_F$). Unless the filter cigarettes individually have fixed $V_F$, their flavor is not steady, which causes quality variation.

The International Organization for Standardization defines a method of measuring the $V_F$. Unexamined Japanese Patent Application Publication No. 2000-39392 discloses a ventilation inspecting apparatus that is employed for this measuring method. The ventilation inspecting apparatus has a plurality of thin packings and suction means. Each of the packings axially partitions the inside of a measuring hole into which a filter cigarette is inserted.

In the center of each packing, there is formed a seal hole with a diameter that is slightly smaller than the external diameter of a filter cigarette. The diameter of the seal hole is expandable. When the filter cigarette is inserted into the measuring hole, the suction means sucks the outer edge of the packing to expand the seal hole, and allows the filter cigarette to pass through the seal hole. At the time of ventilation measurement, the sucking by the suction means is cancelled, so that the seal hole grows small in diameter. The inner circumferential edge of the seal hole is brought into airtight contact with the outer circumferential surface of the filter cigarette.

Once the inner circumferential edge of the seal hole is brought into tight contact with the filter cigarette, first and second chambers are formed in the measuring hole. The filter portion of the filter cigarette is inserted into the first chamber. The end of the filter portion of the filter cigarette is protruding a little into the second chamber. The first and second chambers communicate with each other through the inside of the filter portion.

According to the ventilation inspecting apparatus, while the flow rate of test gas flowing into the first chamber is measured, the test gas is sucked from the second chamber at a predetermined flow rate. Based upon the ratio of these flow rates, filter ventilation is calculated.

However, the packings of the ventilation inspecting apparatus disclosed in the above document are thin, and the diameters of their seal holes are expanded by a sucking force, so that the packings are poor in durability. As a result, the airtightness of the first and second chambers to be separated by the packing is liable to decrease, which widens the measurement error of the $V_F$. Especially, if the airtightness of the packing between the first and second chambers is degraded, part of the test gas supplied into the first chamber directly flows into the second chamber without flowing through the inside of the filter portion. This widens the measurement error of the $V_F$ to a considerable degree. Consequently, nicotine and tar amounts in the filter cigarette cannot be reliably controlled.

The ventilation inspecting apparatus disclosed in the above document is used to carry out a sampling inspection of the $V_F$ of some of the manufactured filer cigarettes. This is because the inspecting apparatus is difficult to be installed into a cigarette manufacturing machine due to its structure. Even if the inspecting apparatus can be installed into the cigarette manufacturing machine, the apparatus is not suitable to inspect the $V_F$ of all the manufactured filter cigarettes because of the low durability of the packings.

DISCLOSURE OF THE INVENTION

It is an object of the present invention to provide an inspecting apparatus capable of accurately measuring ventilation of filter cigarettes for a long period of time.

In order to achieve the above-mentioned object, an apparatus for inspecting ventilation of filter cigarettes according to the present invention has a fluid machine that produces pressure difference between both ends of a test-gas transmitting path including at least one end portion of a filter cigarette to be inspected, a measuring instrument that is provided on the transmitting path and measures a quantity of state of the test gas, a port that is provided on the transmitting path and has an opening larger than an end face of the filter cigarette, the end face being located on a side of the one end portion, a plate-like packing that covers the opening of the port and is relatively pressed with the end face of the filter cigarette, the packing including a hole positioned to a center of the end face pressed thereagainst, an inner circular area surrounding the hole, and an outer circular area surrounding the inner circular area, the outer circular area being elastically deformed more easily than the inner circular area and being brought into tight contact with an outer circumferential edge of the end face pressed against the packing.

According to the ventilation inspecting apparatus of the present invention, when the end face of the filter cigarette is pressed against the packing, the outer circular area of the packing is elastically deformed and is brought into airtight contact with the outer circumferential edge of the end face of the filter cigarette. In short, the outer circular area forms a seal portion that seals between the packing and the end face. At the same time, since the outer circular area is elastically deformed more easily than the inner circular area, the outer circular area is elastically deformed so as to fit a shape of the end face and is brought into surface contact with the outer circumferential edge of the end face while the diameter of the hole is suppressed from being expanded. This surface contact provides high airtightness to between the outer circular area and the end face and also prevents the outer circular area from being soon abraded away. The ventilation inspecting apparatus therefore reliably prevents a test gas leak from occurring at the seal portion of the packing for a long term, and accurately measures ventilation. It is then possible to control filter cigarettes based upon the ventilation in a proper and easy way.

In a preferred aspect, the inner circular area of the packing is thicker than the outer circular area.

In a preferred aspect, the inner circular area of the packing includes a boss portion that is projecting from an opposite face to a face against which the end face is pressed.

In a preferred aspect, the ventilation inspecting apparatus further has a filter assembly. The filter assembly includes a socket hole that is divided by the packing into a first chamber and a second chamber in a state of accommodating the port, the first chamber receiving a filter portion of the filter cigarette as the one end portion; a seal ring that is spaced from the packing within the first chamber and is capable of airtightly surrounding an outer circumferential surface area of the cigarette in the socket hole by being reduced in diameter when pressed in an axial direction of the socket hole; and a sleeve that is slidably fitted in the socket hole so as to be positioned between the packing and the seal ring and transmits pressure applied to an outer edge area of the packing to the seal ring.

The inspecting apparatus according to this aspect is applied to measurement of filter ventilation of a cigarette FT and has the seal ring that partitions off the first chamber in which the filter portion is accommodated.

Since the seal ring is reduced in diameter when pressed and airtightly surrounds the outer circumferential surface area of the filter cigarette, the seal ring needs not to be thin when in a free state. For this reason, if the seal ring is provided with proper thickness, not only airtightness but also great durability are secured, and the seal ring prevents a test gas leak from the first chamber for a long period of time on the opposite side to the second chamber. As described above, the packing and the seal ring have great airtightness and durability, so that the inspecting apparatus is capable of measuring filter ventilation with accuracy for a long term.

In a preferred aspect, the ventilation inspecting apparatus further has a drum. The drum includes an outer circumferential surface on which a transport path for transporting the filter cigarette in a direction orthogonal to an axial direction of the filter cigarette is defined. The first chamber of the socket hole receives the filter portion of the filter cigarette being transported on the transport path.

In the present aspect, the transport path for filter cigarettes is defined on the outer circumferential surface of the drum, and the ventilation of the filter cigarettes is inspected in a transport process. Accordingly, the inspecting apparatus is suitable to be installed in a cigarette manufacturing machine to inspect the filter ventilation of all manufactured filter cigarettes. With the apparatus, therefore, it is possible to measure the filter ventilation of all the filter cigarettes with accuracy for a long term and to control nicotine and tar amounts in the filter cigarettes without fail.

In a preferred aspect, the outer edge area of the packing includes an engaging portion in a face on the side of the first chamber, which couples the packing to the sleeve. In the present aspect, since the packing is coupled to the sleeve that is slidable within the socket hole, the packing can be removed from the socket hole without difficulty. Therefore, the packing is quickly and easily replaced when abraded away. Consequently, when the inspecting apparatus is installed in the cigarette manufacturing machine, it is possible to keep to a minimum a decrease in operating rate of the cigarette manufacturing machine, which is caused by replacement of the packing.

In a preferred aspect, the fluid machine is a compressor that supplies the test gas having prescribed pressure to the first chamber. The measuring instrument is a pressure gauge that measures pressure of the test gas in the second chamber. In the present aspect, the filter ventilation of the filter cigarettes is quickly measured.

BEST MODE OF CARRYING OUT THE INVENTION

Figure 1:
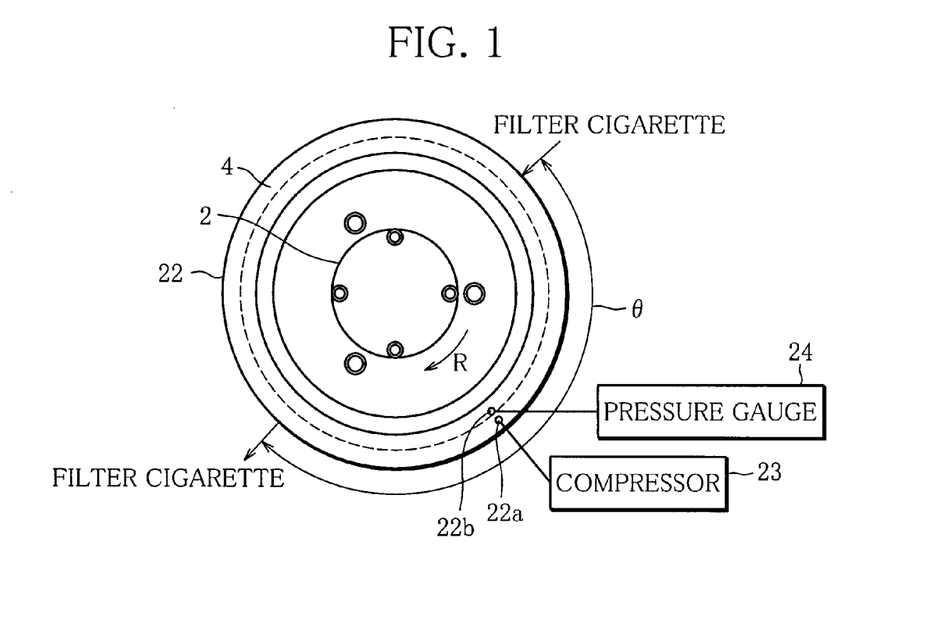
FIG. 1 is a schematic configuration view of an apparatus for inspecting filter ventilation of filter cigarettes according to one embodiment of the present invention, as viewed into a front face.

FIG. 1 shows one end of an apparatus for inspecting filter ventilation of filter cigarettes according to one embodiment of the present invention. The inspecting apparatus is installed, for example, in a filter attachment for attaching filters to cigarettes. Filter cigarettes delivered from the filter attachment all pass through the inspecting apparatus.

The inspecting apparatus has a drum 4 that is rotatable integrally with a drive shaft 2. A prescribed rotation angle range θ of the drum 4 forms a part of a transport path for filter cigarettes (hereinafter, also simply referred to as cigarettes and provided with reference sign FT).

Figure 2:
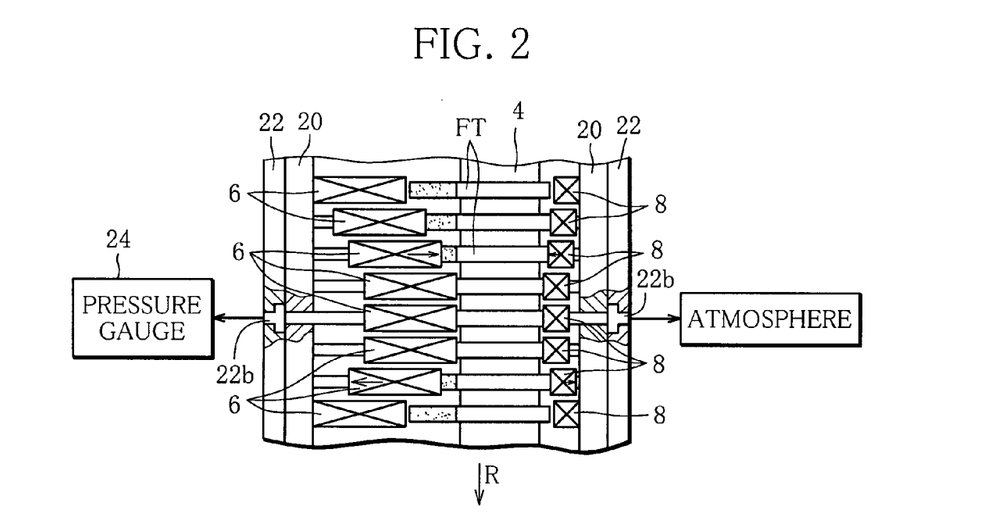
FIG. 2 is a schematic configuration view of a part of the inspecting apparatus of FIG. 1, as viewed into a side face.

To be more precise, a plurality of transport grooves are formed in an outer circumferential surface of the drum 4 at regular intervals in a circumferential direction. The transport grooves are supplied with sucking force of a suction mechanism, not shown, while passing the rotation angle range θ. Due to the sucking force, a cigarette FT is transferred at a start end of the rotation angle range θ, for example, from an end checker drum located immediately upstream of the start end into one of the transport grooves of the drum 4, and is subsequently transported in a rotating direction R orthogonal to an axial direction thereof along with rotation of the drum 4 while retained in the transport groove as illustrated in FIG. 2. When the cigarette FT is transported to reach a terminal end of the rotation angle range θ, the transport groove in which the cigarette FT is retained stops being supplied with the sucking force. The cigarette FT is then transferred, for example, to a carrier drum located immediately downstream.

Disposed near both ends of each of the transport grooves of the drum 4 are a pair of assemblies 6 and 8. The assemblies 6 and 8 rotate with the drum 4, that is, the respective transport grooves.

The inspecting apparatus has a cam mechanism, not shown. Due to operation of the cam mechanism, which is synchronized with the rotation of the drum 4, the assemblies 6 and 8 are attached to and detached from the cigarette FT. More concretely, the assemblies 6 and 8 make one reciprocation between a standby position located away from the cigarette FT and a working position in which the assemblies 6 and 8 are located closer to the cigarette FT by moving forward from the standby position while the cigarette FT is transported in the rotation angle range θ. In this process, the assemblies 6 and 8 are retained in the working position while passing through a given zone of the rotation angle range θ.

Figure 3:
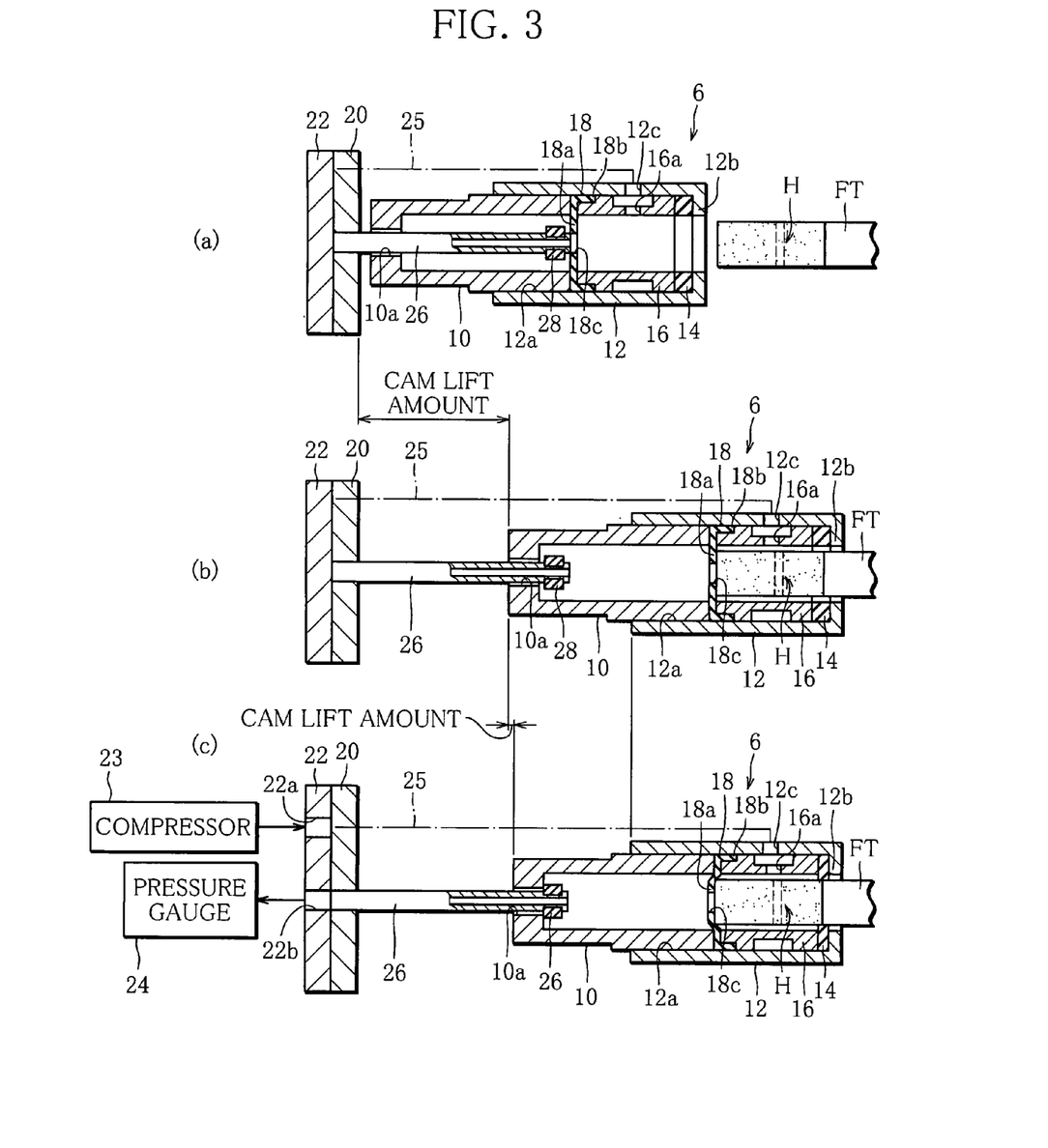
FIG. 3 is a sectional view showing a schematic configuration of an assembly that moves back and forth on the side of a filter portion of a filter cigarette to be inspected, (a) showing the assembly in a standby position, (b) showing the assembly in an intermediate position between the standby position and a working position, and (c) showing the assembly in the working position.

Between the assemblies 6 and 8, the assembly 6 located on the side of a filter portion of the cigarette FT will be described below with reference to FIG. 3(*a*), (*b*) and (*c*). FIG. 3(*a*), (*c*) and (*b*) show the assembly 6 in the standby position, the working position, and an intermediate position between the standby and working positions, respectively.

The assembly 6 includes a movable cylinder 10. One end of the movable cylinder 10 on the side of the drum 4 is open, while a wall at the other end is provided with a pipe hole 10*a* running through the center of the wall. The movable cylinder 10 is so set as to be slidable along an axis of the cigarette FT retained in the corresponding transport groove. The cam mechanism provides a cam lift amount to the movable cylinder 10. The movable cylinder 10 moves forward and backward in proportion to the provided cam lift amount.

The assembly 6 has a seal holder 12 on one end side of the movable cylinder 10. A seal attaching hole 12*a* is formed in the seal holder 12. The seal attaching hole 12*a* extends coaxially with the movable cylinder 10 and runs through the seal holder 12. The movable cylinder 10 is inserted into the seal attaching hole 12*a* through an opening opposite to the drum 4, or the transport grooves. Accordingly, the seal holder 12 and the movable cylinder 10 are partially fitted in each other, and the seal holder 12 is slidably supported by the movable cylinder 10.

The filter portion of the cigarette FT is inserted in and pulled out from the seal attaching hole 12*a* through an opening located on the side of the drum 4. When the assembly 6 is situated between the intermediate position and the working position, the filter portion is positioned within the seal attaching hole 12*a*.

The seal holder 12 has an inward flange 12*b* in an opening edge of the seal attaching hole 12*a* on the side of the drum 4. A seal ring 14 made of silicone rubber is fitted in an inner circumferential surface of the seal attaching hole 12*a* adjacently to the inward flange 12*b*.

The seal ring 14 is made of elastic material. When the seal ring 14 is in a free state, as illustrated in FIGS. 3(*a*) and (*b*), an internal diameter of the seal ring 14 is larger than an external diameter of the cigarette FT. When compressed in an axial direction, however, the seal ring 14 is elastically deformed to expand inward in a radial direction as illustrated in FIG. 3(*c*). The expanded seal ring 14 airtightly surrounds an outer circumferential surface of the cigarette FT at an end portion of the filter portion adjacent to a cigarette portion or near a border between the filter portion and the cigarette portion.

An inner cylinder 16 is slidably fitted in the inner circumferential surface of the seal attaching hole 12*a*. The seal ring 14 is sandwiched between the inner cylinder 16 and the inner flange 12*b*. The inner cylinder 16 has an internal diameter larger than the external diameter of the cigarette FT. Formed in an outer circumferential surface of the inner cylinder 16 is a circumferential groove. A vent hole 16*a* piercing through the inner cylinder 16 is open in a bottom surface of the circumferential groove. Formed in the seal holder 12 is a radial direction hole 12*c* extending from the seal attaching hole 12*a* in an outward direction. The radial direction hole 12*c* and the circumferential groove of the inner cylinder 16 coincide with each other, as viewed in an axial direction of the seal attaching hole 12*a*.

Disposed between the movable cylinder 10 and the inner cylinder 16 is a packing 18 made of silicone rubber. When the movable cylinder 10 moves forward, the cam lift amount is transmitted to the inward flange 12*b* through the packing 18, the inner cylinder 16 and the seal ring 14, and the seal holder 12 also moves forward with the movable cylinder 10.

However, the inspecting apparatus has a stopper, not shown, which regulates the forward movement of the seal holder 12 while the assembly 6 advances from the intermediate position to the working position. Therefore, when the assembly 6 advances from the intermediate position to the working position, the movable cylinder 10 is pressed into the seal holder 12. By so doing, the movable cylinder 10 provides pressure to the seal ring 14 through the inner cylinder 16, whereby the seal ring 14 is compressed.

The inspecting apparatus further has an engaging member, not shown. The engaging member engages the movable cylinder 10 and the seal holder 12 with each other and causes the seal holder 12 to move backward with the movable cylinder 10 while the assembly 6 retreats from the intermediate position to the standby position.

The packing 18 comprises a disk portion 18*a* as a main body and a cylinder portion 18*b* that continues integrally to an outer circumferential edge of the disk portion 18*a*. An external diameter of an end portion of the inner cylinder 16 is smaller than an internal diameter of the seal attaching hole 12*a*. The cylinder portion 18*b* is fitted in the end portion of the inner cylinder 16 from the outside. As a result, the packing 18 is fixed to the inner cylinder 16. An outer circumferential surface of the cylinder portion 18*b* is in slidable and airtight contact with the inner circumferential surface of the seal attaching hole 12*a*.

The disk portion 18*a* is fitted into the seal attaching hole 12*a*. The outer circumferential edge of the disk portion 18*a* is also in slidable and airtight contact with the inner circumferential surface of the seal attaching hole 12*a*. The disk portion 18*a* divides the inside of the seal attaching hole 12*a* into first and second chambers. The first chamber receives the filter portion of the cigarette FT, whereas the second chamber is inserted with a tip end-side portion of the movable cylinder 10.

Formed in the center of the disk portion 18*a* is a hole 18*c*. The hole 18*c* has an internal diameter smaller than the external diameter of the cigarette FT. When the assembly 6 moves from the intermediate position to the working position, the hole 18*c* is approximately positioned in the center of an end face of the filter portion.

Figure 4:
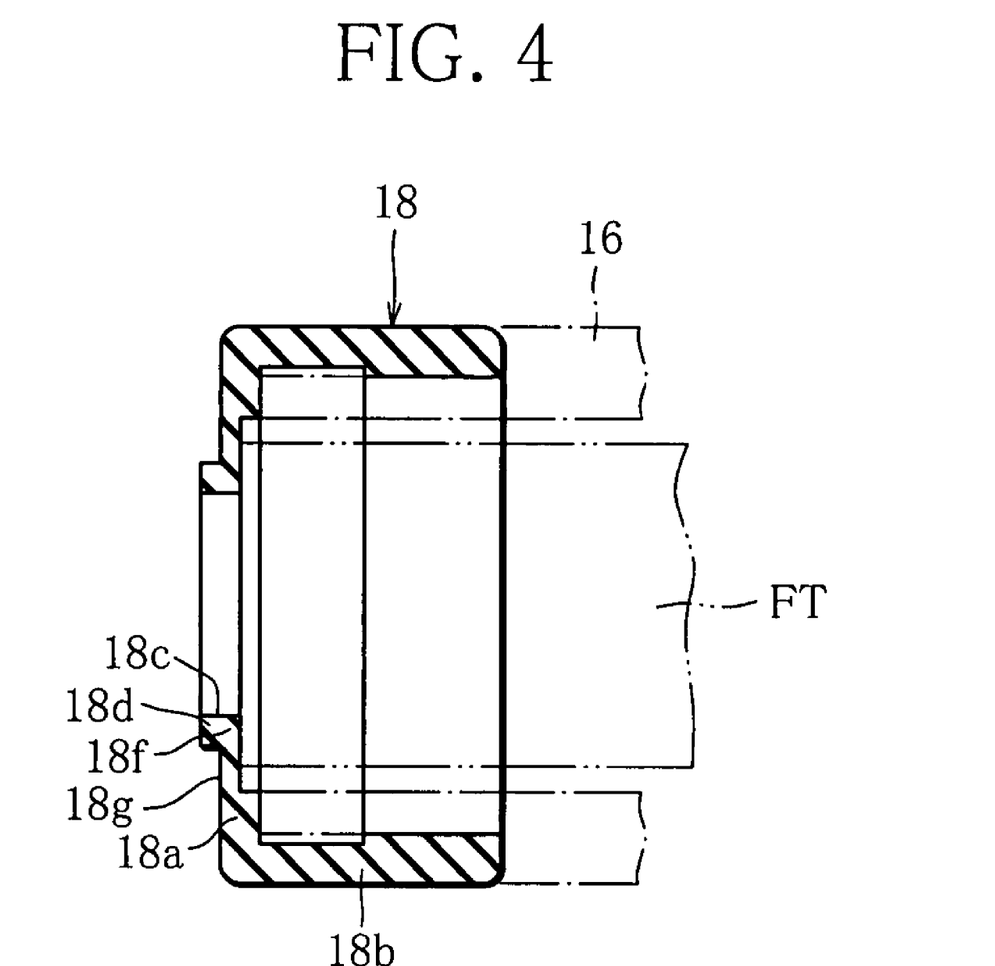
FIG. 4 is a sectional view showing in an enlarged scale a packing applied to the assembly of FIG. 3.

The disk portion 18*a* has a thick portion in a ring-shaped area (hereinafter, referred to as an inner circular area and provided with reference sign 18*f*) surrounding the hole 18*c*. To be more concrete, a boss portion 18*d* is formed on a surface of the disk portion 18*a* on the side of the movable cylinder 10 along a circumferential edge of the hole 18*c* as illustrated in FIG. 4 in an enlarged scale. The boss portion 18*d* has an external diameter smaller than the external diameter of the filter portion of the cigarette FT. The inner circular area 18*f* of the disk portion 18*a* has thickness that is partially increased due to the boss portion 18*d*, as viewed in a radial direction.

In other words, the inner circular area 18f is thicker than a ring-shaped area (hereinafter, referred to as an outer circular area and provided with reference sign 18g) surrounding the inner circular area 18f. The outer circular area 18g has an external diameter larger than the external diameter of the cigarette FT. When the assembly 6 moves from the intermediate position to the working position, the outer circular area 18g is pressed with an external circumferential edge of the end face of the filter portion from the direction of the first chamber. An opening edge of the movable cylinder 10 is brought into airtight contact from the direction of the second chamber to an outer edge area of the disk portion 18a, which is located more outside than the outer circular area 18g.

The inspecting apparatus further has a gas input/output mechanism. The gas input/output mechanism performs input and output of test gas with respect to the assembly 6. More specifically, as illustrated in FIG. 2, the gas input/output mechanism includes a rotary ring 20 and a stationary ring 22. The rings 20 and 22 are arranged coaxially with the drum 4. The assembly 6 is situated between the rotary ring 20 and the drum 4. The rotary ring 20 is in airtight and slidable contact with the stationary ring 22 located on the opposite side to the drum 4.

The stationary ring 22 is unrotatably installed and has an input hole 22a and an output hole 22b arranged in predetermined circumference-directional positions to be spaced from each other in a radial direction (see FIGS. 1 and 3). The input hole 22a and the output hole 22b run through the stationary ring 22 in an axial direction. Both ends of the input and output holes 22a and 22b are open in both sides of the stationary ring 22.

Formed in one side of the stationary ring 22, with which the rotary ring 20 is in contact, are two circular arc-shaped slots. Radial direction positions of these slots coincide with respective opening positions of the input hole 22a and the output hole 22b.

End portions of the input hole 22a and the output hole 22b, which are open in the other side of the stationary ring 22, are connected through tubes to a compressor 23 and a pressure gauge 24, respectively. The compressor 23 is capable of supplying compressed gas having prescribed pressure as test gas, whereas the pressure gauge 24 is capable of measuring pressure of the test gas.

The rotary ring 20 is installed to be capable of rotating integrally with the drum 4 and the assembly 6. A pair of input pipe 25 and output pipe 26 extend between the rotary ring 20 and each of the assemblies 6 parallel with the axis of the rotary ring 20. Base ends of the pipes 25 and 26 are fastened to the rotary ring 20 and are open in one side of the rotary ring 20, which is brought into slidable contact with the stationary ring 22. The input and output pipes 25 and 26 are spaced from each other in a radial direction of the rotary ring 20. Radial direction positions of the input and output pipes 25 and 26 coincide with radial direction positions of the input and output holes 22a and 22b of the stationary ring 22, respectively.

The output pipe 26 has prescribed length. A tip end-side portion of the output pipe 26 is inserted in the movable cylinder 10 through the pipe hole 10a. A circumferential groove is formed in the output pipe 26 closely to the tip end thereof, and a V ring 28 is fitted into the circumferential groove from the outside. Therefore, the V ring 28 is always positioned near the tip end of the output pipe 26. When the assembly 6 is in the standby position, the V ring 28 is relatively situated near the open end of the movable cylinder 10. When the assembly 6 is in the working position, the V ring 28 is pressed against the end wall of the movable cylinder 10 and airtightly blocks up a gap of between the pipe hole 10a and the output pipe 26.

Unlike the output pipe 26, the input pipe 25 is capable of expansion and contraction. A tip end of the input pipe 25 is connected to the radial direction hole 12c of the seal holder 12, and the input pipe 25 extends/contracts in response to movement of the seal holder 12.

An assembly 8 located on the side of the cigarette portion of the cigarette FT has a similar configuration to that of the assembly 6 located on the side of the filter portion. Therefore, identical components are provided with identical reference signs, and descriptions thereof will be omitted. Hereinafter, differences between the assemblies 6 and 8 will be described.

Figure 5:
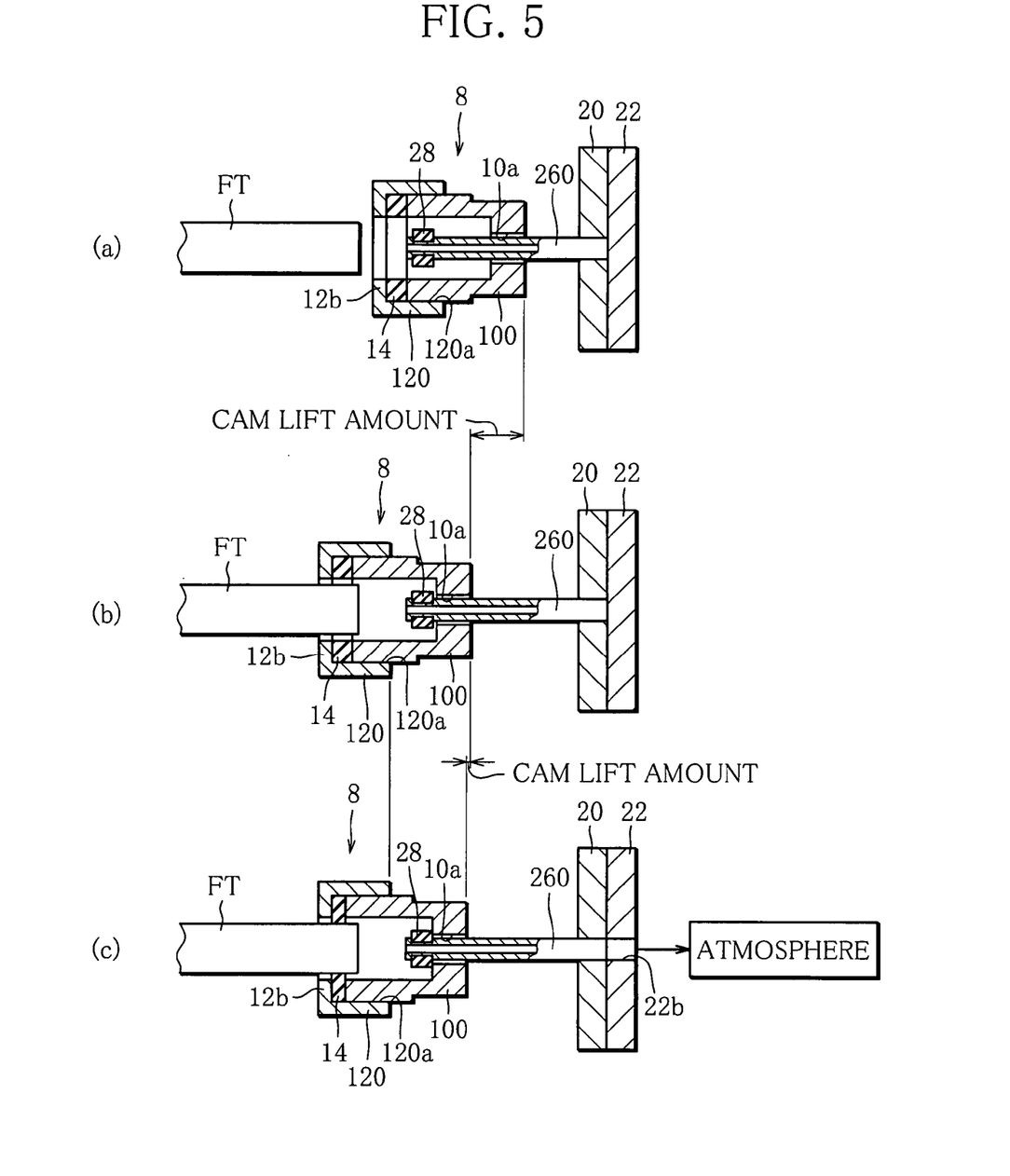
FIG. 5 is a sectional view showing a schematic configuration of the assembly that is attached to and detached from a cigarette portion of the filter cigarette to be inspected in the inspecting apparatus of FIG. 2, (a) showing the assembly in a standby position, (b) showing the assembly in an intermediate position between the standby position and a working position, and (c) showing the assembly in the working position.

In respect of the assembly 8, only a tip end of the cigarette portion is inserted therein and pulled out therefrom as illustrated in FIG. 5(a), (b) and (c). There is no chamber corresponding to the first chamber of the assembly 6. For this reason, in the assembly 8, a cam lift amount between a standby position and an intermediate position is small. Moreover, a movable cylinder 100, a seal holder 120, a seal attaching hole 120a, and an output pipe 260 are short in length. The radial direction hole 12c is not formed in the seal holder 120. The inner cylinder 16 and the packing 18 are not disposed within the seal attaching hole 120a.

A gas input/output mechanism for the assembly 8 simply outputs test gas from the assembly 8. That is to say, the gas input/output mechanism does not include the input pipe 25, the input hole 22a, the compressor 23, and the pressure gauge 24. When the assembly 8 is in a working position, the inside of the movable cylinder 100 communicates with the atmosphere through the output pipe 260 and the output hole 22b.

Hereinafter, a method for measuring filter ventilation of the cigarette FT using the inspecting apparatus will be described.

When the assembly 6 is in the working position, the filter portion of the cigarette FT is accommodated in the first chamber partitioned off within the seal attaching hole 12a. At the same time, the seal ring 14 seals between the inner circumferential surface of the seal attaching hole 12a and the outer circumferential surface of the cigarette FT in the vicinity of the border between the filter portion and the cigarette portion. The disk portion 18a of the packing 18 seals between the outer circumferential edge of the end face of the filter portion and the inner circumferential surface of the seal attaching hole 12a.

In this state, the compressed gas having the prescribed pressure is supplied from the compressor 23 to the circumference of the filer portion in the first chamber through the input hole 22a, the input pipe 25, the radial direction hole 12c, the circumferential groove of the inner cylinder 16, and the vent hole 16a. The pressure applied onto the circumference of the filter portion rises up to the pressure of the compressed gas. Due to the pressure of the compressed gas, the compressed gas supplied into the first chamber flows into the inside of the filter portion through a line of perforations H (see FIG. 3) formed in the outer circumferential surface of the filter portion, and runs through the cigarette FT toward both the ends of the cigarette FT. The compressed gas that has run toward the end face of the filter portion flows into the second chamber, or the movable cylinder 10, through the hole 18c of the packing 18, whereby the pressure in the movable cylinder 10 is increased. The increased pressure in the movable cylinder 10 is guided outside the assembly 6 through the output pipe 26 and the output hole 22b and is measured by the pressure gauge 24 connected to the movable cylinder 10. The compressed gas that has run toward the end face of the cigarette portion is released into the atmosphere through the assembly 8.

The filter ventilation $V_F$ is given by the following expression:

$$V_F = P2/P1$$

where P1 is the pressure of the compressed gas supplied from the compressor 23 into the first chamber, and P2 is the pressure measured by the pressure gauge 24. By comparing a value of the calculated $V_F$ with a target value, a judgment is made as to whether the $V_F$ of the cigarette FT to be inspected is defective or nondefective. For instance, a cigarette FT that is judged defective is removed from the transport path and discarded, so that nicotine and tar amounts of cigarettes FT to be shipped are controlled to be virtually uniform.

With the above-described inspecting apparatus, the packing 18 is in tight contact, not with the outer circumferential surface of the filter portion, but with the end face of the filter portion. Since the packing 18 is in surface contact with the end face of the filter portion, it is a matter of course that the outer circumferential surface of the filter portion is prevented by the packing 18 from getting crinkled. Furthermore, the outer circular area 18g, namely the seal portion, of the packing 18 is not soon abraded away. Consequently, the packing 18 prevents a compressed gas leak from occurring in between the first and second chambers for a long period of time.

In the packing 18, the boss portion 18d thickens a part of the inner circular area 18f, to thereby form a thick portion in the disk portion 18a. In this case, when the disk portion 18a is pressed by the end face of the filter portion, the outer circular area 18g located more outside than the thick portion as viewed in a radial direction is elastically deformed while the hole 18c is prevented from being expanded in diameter because of the thick portion. The outer circular area 18g that has been elastically deformed is brought into tight contact with the outer circumferential edge of the end face of the filter portion without leaving a gap. This improves airtightness at the end face of the filter portion. The inspecting apparatus therefore makes it possible to upgrade measurement accuracy of the $V_F$ and to reliably control the nicotine and tar amounts of the cigarettes FT.

According to the inspecting apparatus, the seal ring 14 is reduced in diameter when pressed, and airtightly surrounds the outer circumferential surface area of the cigarette FT. The seal ring 14, when in a free state, then needs not to be as thin as a conventional packing. As a result, durability of the seal ring 14 is easily and sufficiently secured by providing the seal ring 14 with proper thickness. Consequently, the seal ring 14 prevents a compressed gas leak from occurring in the first chamber on the opposite side to the second chamber for a long term.

As described above, with the inspecting apparatus, since a compressed gas leak is prevented from occurring in the first chamber by the packing 18 and the seal ring 14, the filter ventilation of the cigarettes FT is accurately measured for a long period of time.

The present invention is not limited to the one embodiment described above. For instance, the transport path for the cigarettes FT may be constituted by a transport device other than the drum 4. Configuration of the cam mechanism and that of the gas input/output mechanism are not particularly limited, either.

The inspecting apparatus of the one embodiment is installed in a filter cigarette manufacturing machine and is used to inspect the filter ventilation of all the manufactured cigarettes FT. The inspecting apparatus, however, may be independently assembled for being applied to a sampling inspection of the cigarettes FT. In order to control the nicotine and tar amounts of the cigarettes FT, however, it is preferable that the inspecting apparatus be installed in the filter cigarette manufacturing machine, and that all the cigarettes FT in the transport process undergo the inspection.

In the inspecting apparatus of the one embodiment, material of the seal ring 14 and the packing 18 is silicone rubber. The material, however, is not particularly limited, and can be properly selected among natural rubber, synthetic rubber, a gel substance, etc.

Figure 6:
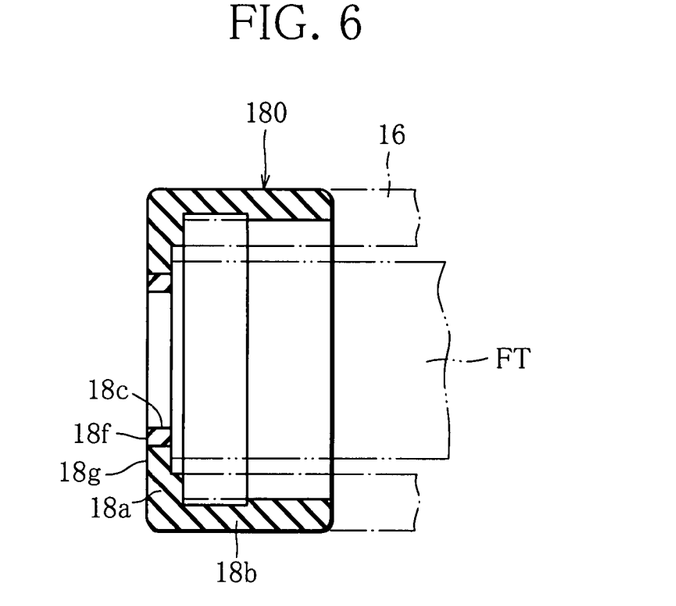
FIG. 6 is a sectional view showing a packing of a modification example in an enlarged scale.

Material applied to the packing 18 is not limited to one. The inner circular area 18f and the outer circular area 18g of the disk portion 18a may be integrally molded using materials that are different in elasticity modulus as a packing 180 illustrated in FIG. 6 so that the outer circular area 18g is elastically deformed more easily than the inner circular area 18f. Stated differently, material having higher elasticity modulus than the material of the inner circular area 18f is used for the outer circular area 18g. More preferably, more flexible material is used for the outer circular area 18g in order to enhance sealing property.

Figure 7:
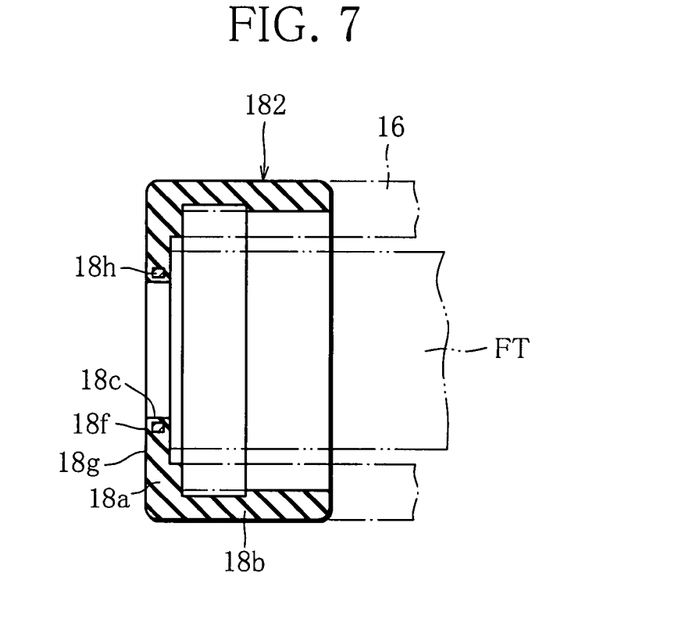
FIG. 7 is a sectional view showing a packing of another modification example in an enlarged scale.

As a packing 182 shown in FIG. 7, instead of the boss portion 18d, for example, a metal ring 18h may be embedded in the inner circular area 18f as a core material by insert molding.

Nevertheless, considering the sealing property and easiness of fabrication, it is preferable that the boss portion 18d protruding in the opposite direction to the cigarette FT be formed in the inner circular area 18f of the packing 18.

Although the packing 18 is used in the inspecting apparatus of the one embodiment, another seal ring (hereinafter, referred to as a second seal ring) may be placed between the movable cylinder 10 and the inner cylinder 16 instead of the packing 18. The second seal ring may be expanded at the time of measurement of the $V_F$ so as to airtightly surround an outer circumferential surface of the filter portion near the end face of the filter portion. Contact area of the seal portion of the packing 18 and the end face of the filter portion is larger than that of the second seal ring and the outer circumferential surface of the filter portion. Therefore, the packing 18 is higher in durability than the second seal ring, and also separates the first and second chambers from each other more airtightly than the second seal ring does. For this reason, it is preferable that the packing 18 be used to separate the first and second chambers from each other. Especially, a great factor of an error in measurement of the $V_F$ is the fact that part of the test gas supplied into the first chamber does not flow through the inside of the filter portion but leaks to run directly into the second chamber. With the packing 18, however, such a test gas leak is prevented without fail, and the measurement accuracy of the $V_F$ is improved.

In the inspecting apparatus of the one embodiment, the packing 18 has the cylinder portion 18b on the side of the first chamber and is fixed to the inner cylinder 16 through the cylinder portion 18b. It is possible, however, to cause the movable cylinder 10 and the inner cylinder 16 to sandwich the disk portion 18a therebetween, instead of providing the cylinder portion 18b to the packing 18. Even so, if the cylinder portion 18b is fixed to the inner cylinder 16, the packing 18 can be easily taken out of the seal attaching hole 12a, so that the packing 18 can be replaced quickly and easily when abraded away.

Figure 8:
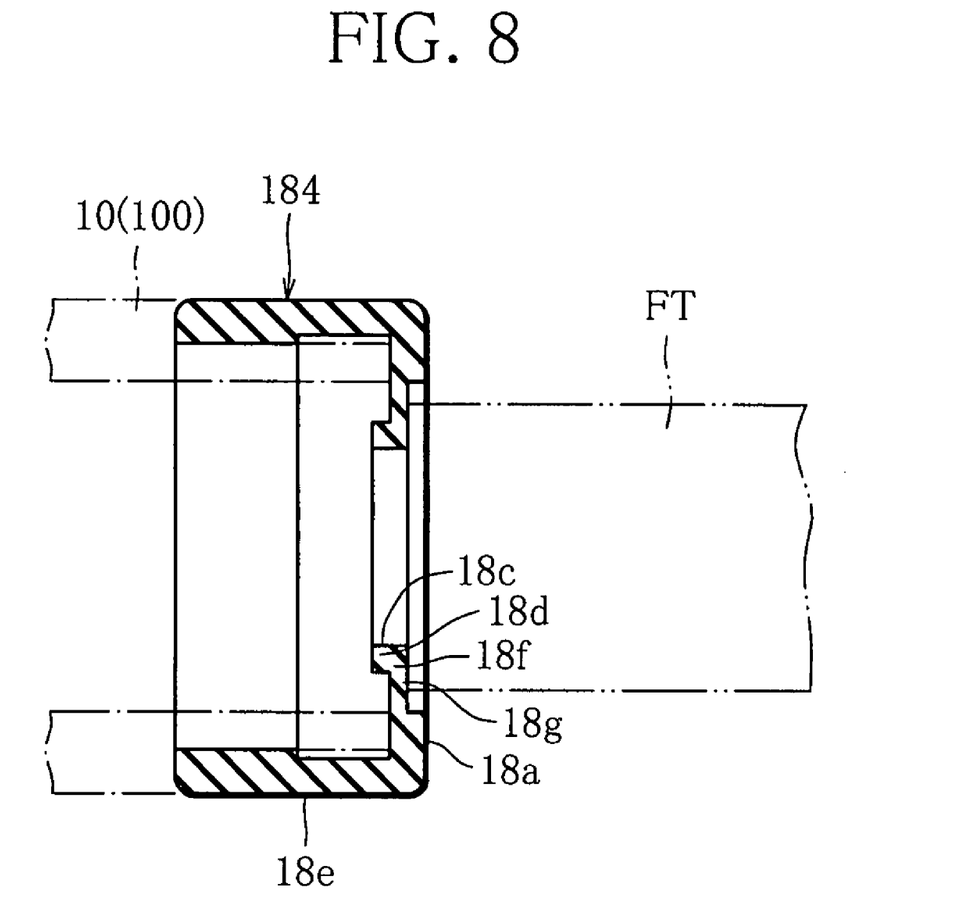
FIG. 8 is a sectional view showing a packing of still another modification example in an enlarged scale.

It is also possible, as a packing 184 shown in FIG. 8, to integrally form a cylinder portion 18e on a face of the disk portion 18a which is on the second chamber side, instead of the cylinder portion 18b, and to fit the cylinder portion 18e in the movable cylinder 10.

Instead of the seal ring 14, the packing 184 may be applied to the assembly 8 located on the side of the cigarette portion of the cigarette FT, and the cylinder portion 18e may be fixed to the movable cylinder 100.

In the inspecting apparatus of the one embodiment, the filter ventilation is calculated based upon the pressure difference (P2/P1) at the time point when the first chamber is applied with pressure by using the compressor. Alternatively, the filter ventilation may be calculated based upon pressure difference at the time point when the second chamber is sucked by using a suction device.

The filter ventilation may be calculated based upon a flow rate ratio or flow velocity ratio. To this end, the test gas of a predetermined flow rate is supplied to the assembly 6 by the compressor 23, and a flowmeter is connected to the output hole 22b. On the other hand, time required before the flow rate ratio is stabilized is longer than time required before the pressure ratio is stabilized, so that inspection time is prolonged if the filter ventilation is inspected based upon the flow rate ratio. Therefore, the filter ventilation is preferably calculated based upon the pressure ratio as in the inspecting apparatus of the one embodiment.

The inspecting apparatus is also applicable not only to the measurement of the filter ventilation but that of entire ventilation and wrapper ventilation of the cigarette FT by changing the arrangement of the fluid machine such as the compressor and the measuring instrument such as the pressure gauge.

The invention claimed is:

1. An apparatus for inspecting ventilation of filter cigarettes, comprising:
    a fluid machine for producing pressure difference between both ends of a test-gas transmitting path including at least one end portion of a filter cigarette to be inspected;
    a measuring instrument provided on the transmitting path, for measuring a quantity of the test gas;
    a port provided in the transmitting path, for receiving the one end portion of the filter cigarette from one opening end of said port; and
    a plate-like packing covering another opening end of said port, for being pressed with the end face of the filter cigarette, the packing including a hole positioned in a center thereof, a flat inner circular area surrounding the hole, and a flat outer circular area surrounding the inner flat circular area, the flat outer circular area being elastically deformable more easily than the flat inner circular area, wherein, when a filter cigarette is inspected, the flat inner circular area of the plate-like packing is brought into surface contact with the end face of the filter cigarette, and the flat outer circular area of the plate-like packing is brought into tight contact with the outer circumferential edge of the end face of the filter cigarette.

2. The apparatus for inspecting ventilation of filter cigarettes according to claim 1, wherein the inner circular area of the packing is thicker than the outer circular area.

3. The apparatus for inspecting ventilation of filter cigarettes according to claim 2, wherein the inner circular area of the packing includes a boss portion that is projecting from an opposite face to a face against which the end face is pressed.

4. The apparatus for inspecting ventilation of filter cigarettes according to claim 1, further having a socket assembly, wherein:

the socket assembly includes:
    a socket hole that is divided by the packing into a first chamber and a second chamber in a state of accommodating the port, the first chamber receiving a filter portion of the filter cigarette as the one end portion;
    a seal ring that is spaced from the packing within the first chamber and is capable of airtightly surrounding an outer circumferential surface area of the cigarette in the socket hole by being reduced in diameter when pressed in an axial direction of the socket hole; and
    a sleeve that is slidably fitted in the socket hole so as to be positioned between the packing and the seal ring and transmits pressure applied to an outer edge area of the packing to the seal ring.

5. The apparatus for inspecting ventilation of filter cigarettes according to claim 4, further having a drum, wherein:
    the drum includes an outer circumferential surface on which a transport path for transporting the filter cigarette in a direction orthogonal to an axial direction of the filter cigarette is defined; and
    the first chamber of the socket hole receives the filter portion of the filter cigarette being transported on the transport path.

6. The apparatus for inspecting ventilation of filter cigarettes according to claim 5, wherein:
    the outer edge area of the packing includes an engaging portion in a face on the side of the first chamber, which couples the packing to the sleeve.

7. The apparatus for inspecting ventilation of filter cigarettes according to claim 4, wherein:
    the fluid machine is a compressor that supplies the test gas having prescribed pressure to the first chamber, and the measuring instrument is a pressure gauge that measures pressure of the test gas in the second chamber.

8. An apparatus for inspecting ventilation of filter cigarettes, comprising:
    a fluid machine for producing pressure difference between both ends of a test-gas transmitting path including at least one end portion of a filter cigarette to be inspected;
    a measuring instrument provided on the transmitting path, for measuring a quantity of the test gas;
    a port provided in the transmitting path, for receiving the one end portion of the filter cigarette from one opening end of said port; and
    a plate-like packing covering another opening end of said port, for being brought into close contact and pressed with the end face of the filter cigarette, the packing including a hole positioned in a center thereof, a flat inner circular area surrounding the hole and a flat outer circular area surrounding the inner flat circular area, the flat outer circular area being elastically deformable more easily than the flat inner circular area, wherein, when a filter cigarette is inspected, the flat inner circular area of the plate-like packing is brought into surface contact with the end face of the filter cigarette, and the flat outer circular area of the plate-like packing is brought into tight contact with the outer circumferential edge of the end face of the filter cigarette for providing high sealing performance to reduce the force with which the packing is brought into close contact with the filter cigarette.

* * * * *